(12) United States Patent
Nau, Jr.

(10) Patent No.: US 11,786,304 B2
(45) Date of Patent: *Oct. 17, 2023

(54) MEDICAL DEVICES AND METHODS INCORPORATING FRUSTRATED TOTAL INTERNAL REFLECTION FOR ENERGY-EFFICIENT SEALING AND CUTTING OF TISSUE USING LIGHT ENERGY

(71) Applicant: Covidien LP, Mansfield, MA (US)

(72) Inventor: William H. Nau, Jr., Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 279 days.

This patent is subject to a terminal disclaimer.

(21) Appl. No.: 17/145,584

(22) Filed: Jan. 11, 2021

(65) Prior Publication Data

US 2021/0128239 A1 May 6, 2021

Related U.S. Application Data

(63) Continuation of application No. 16/297,313, filed on Mar. 8, 2019, now Pat. No. 10,893,908, which is a
(Continued)

(51) Int. Cl.
*A61B 18/22* (2006.01)
*A61B 18/00* (2006.01)
(Continued)

(52) U.S. Cl.
CPC ............ *A61B 18/22* (2013.01); *A61B 18/201* (2013.01); *A61B 18/1442* (2013.01);
(Continued)

(58) Field of Classification Search
CPC ....... A61B 18/22; A61B 18/20; A61B 18/201; A61B 18/1442; A61B 18/1445;
(Continued)

(56) References Cited

U.S. PATENT DOCUMENTS 4,126,136 A 11/1978 Auth et al.
4,757,425 A 7/1988 Waltz
(Continued)

FOREIGN PATENT DOCUMENTS

EP 0480293 A1 4/1992
EP 1891891 A1 2/2008
(Continued)

OTHER PUBLICATIONS

European Search Report issued in corresponding patent application No. EP 15 16 1888, dated Jul. 13, 2015.
(Continued)

*Primary Examiner* — Timothy J Neal
*Assistant Examiner* — William B Chou
(74) *Attorney, Agent, or Firm* — Carter, DeLuca & Farrell LLP

(57) ABSTRACT

A medical instrument includes two jaw members, at least one of which creates conditions of frustrated total internal reflection at a tissue-contacting surface when tissue is grasped between the two jaw members. The first jaw member may include an optical element having a tissue-contacting surface. The medical instrument also includes a light source that provides a light beam for sealing tissue. The light source is positioned so that the light beam is totally internally reflected from an interface between the tissue-contacting surface and air when tissue is not grasped by the jaw members. When tissue is grasped by the jaw members, at least a portion of the light beam is transmitted through that portion of the tissue-contacting surface that is in contact with the tissue. The light source may be movably coupled to a jaw member to scan the light beam and/or to change the incident angle based on optical properties of the tissue.

20 Claims, 11 Drawing Sheets

Related U.S. Application Data continuation of application No. 13/903,091, filed on May 28, 2013, now Pat. No. 10,226,297.

(60) Provisional application No. 61/697,671, filed on Sep. 6, 2012.

(51) Int. Cl.
*A61B 18/20* (2006.01)
*A61B 18/14* (2006.01)

(52) U.S. Cl.
CPC ....... *A61B 18/1445* (2013.01); *A61B 18/1447* (2013.01); *A61B 2018/0063* (2013.01); *A61B 2018/00202* (2013.01); *A61B 2018/00345* (2013.01); *A61B 2018/00601* (2013.01); *A61B 2018/00648* (2013.01); *A61B 2018/00666* (2013.01); *A61B 2018/00702* (2013.01); *A61B 2018/00732* (2013.01); *A61B 2018/00791* (2013.01); *A61B 2018/00875* (2013.01); *A61B 2018/00904* (2013.01); *A61B 2018/2065* (2013.01); *A61B 2018/2272* (2013.01)

(58) Field of Classification Search
CPC ........ A61B 18/1447; A61B 2018/0063; A61B 2018/145
See application file for complete search history.

(56) References Cited

U.S. PATENT DOCUMENTS

| | | | |
|---|---|---|---|
| 4,760,845 A | 8/1988 | Kovalcheck |
| 5,055,983 A | 10/1991 | Hunold et al. |
| 5,147,356 A | 9/1992 | Bhatta |
| 5,169,396 A | 12/1992 | Dowlatshahi et al. |
| 5,209,748 A | 5/1993 | Daikuzono |
| 5,261,410 A | 11/1993 | Alfano et al. |
| 5,336,221 A | 8/1994 | Anderson |
| 5,342,358 A | 8/1994 | Daikuzono |
| 5,470,331 A | 11/1995 | Daikuzono |
| 5,586,982 A | 12/1996 | Abela |
| 5,598,843 A | 2/1997 | Caisey et al. |
| 5,762,609 A | 6/1998 | Benaron et al. |
| 5,769,791 A | 6/1998 | Benaron et al. |
| 5,810,010 A | 9/1998 | Anbar |
| 5,953,477 A | 9/1999 | Wach et al. |
| 6,002,958 A | 12/1999 | Godik |
| 6,039,729 A | 3/2000 | Durville et al. |
| 6,053,909 A | 4/2000 | Shadduck |
| 6,086,586 A | 7/2000 | Hooven |
| 6,122,042 A | 9/2000 | Wunderman et al. |
| 6,175,768 B1 | 1/2001 | Arndt et al. |
| 6,221,069 B1 | 4/2001 | Daikuzono |
| 6,385,474 B1 | 5/2002 | Rather et al. |
| 6,508,816 B2 | 1/2003 | Shadduck |
| 6,776,760 B2 | 8/2004 | Marmarelis |
| 6,869,430 B2 | 3/2005 | Balbierz et al. |
| 6,993,383 B2 | 1/2006 | Assenheimer |
| 7,414,724 B2 | 8/2008 | Eckert et al. |
| 7,598,088 B2 | 10/2009 | Balas |
| 7,662,152 B2 | 2/2010 | Sharareh et al. |
| 7,775,103 B2 | 8/2010 | Veerasamy |
| 7,949,387 B2 | 5/2011 | Khoobehi et al. |
| 8,221,418 B2 | 7/2012 | Prakash et al. |
| 8,241,282 B2 | 8/2012 | Unger et al. |
| 8,388,543 B2 | 3/2013 | Chon et al. |
| 8,444,636 B2 | 5/2013 | Shadduck et al. |
| 10,226,297 B2 | 3/2019 | Nau, Jr. |
| 10,893,908 B2 | 1/2021 | Nau, Jr. |
| 2003/0078477 A1 | 4/2003 | Kang et al. |
| 2005/0080413 A1 | 4/2005 | Canady |
| 2005/0131390 A1 | 6/2005 | Heinrich et al. |
| 2005/0197655 A1 | 9/2005 | Telfair |
| 2005/0234437 A1 | 10/2005 | Baxter et al. |
| 2006/0089637 A1 | 4/2006 | Werneth et al. |
| 2006/0282068 A1 | 12/2006 | Griffin et al. |
| 2007/0225695 A1 | 9/2007 | Mayer et al. |
| 2007/0270792 A1 | 11/2007 | Hennemann et al. |
| 2008/0077200 A1 | 3/2008 | Bendett et al. |
| 2008/0132886 A1 | 6/2008 | Cohen et al. |
| 2008/0221409 A1 | 9/2008 | Hoarau |
| 2008/0247594 A1 | 10/2008 | Leclear et al. |
| 2009/0228019 A1 | 9/2009 | Gross |
| 2009/0287194 A1 | 11/2009 | Gertz et al. |
| 2009/0318912 A1 | 12/2009 | Mayer et al. |
| 2010/0016810 A1 | 1/2010 | Drews et al. |
| 2010/0049187 A1 | 2/2010 | Carlton et al. |
| 2010/0160904 A1 | 6/2010 | McMillan et al. |
| 2010/0217258 A1 | 8/2010 | Floume et al. |
| 2011/0190749 A1 | 8/2011 | McMillan et al. |
| 2011/0251605 A1 | 10/2011 | Hoarau et al. |
| 2012/0004547 A1 | 1/2012 | Harks |
| 2012/0130256 A1 | 5/2012 | Buysse et al. |
| 2012/0150170 A1 | 6/2012 | Buysse et al. |
| 2012/0226272 A1 | 9/2012 | Chernov et al. |
| 2012/0296205 A1 | 11/2012 | Chernov et al. |
| 2012/0296238 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2013/0253489 A1 | 9/2013 | Nau, Jr. et al. |
| 2014/0121508 A1 | 5/2014 | Latimer et al. |
| 2014/0288541 A1 | 9/2014 | Eshkol et al. |
| 2015/0114092 A1 | 4/2015 | Paidosh |
| 2017/0212295 A1 | 7/2017 | Vasylyev |

FOREIGN PATENT DOCUMENTS

| | | |
|---|---|---|
| WO | 8503781 A1 | 8/1985 |
| WO | 9408526 A1 | 4/1994 |
| WO | 2008024022 A1 | 2/2008 |
| WO | 20090005850 A1 | 1/2009 |
| WO | 2012158788 A1 | 11/2012 |

OTHER PUBLICATIONS

Search Report dated Nov. 20, 2013, in corresponding European patent application No. 13183113.3.

MEDICAL DEVICES AND METHODS INCORPORATING FRUSTRATED TOTAL INTERNAL REFLECTION FOR ENERGY-EFFICIENT SEALING AND CUTTING OF TISSUE USING LIGHT ENERGY

CROSS REFERENCE TO RELATED APPLICATION

The present application is a continuation of U.S. patent application Ser. No. 16/297,313, filed on Mar. 8, 2019, which is a continuation of U.S. patent application Ser. No. 13/903,091, filed on May 28, 2013, now U.S. Pat. No. 10,226,297, which claims the benefit of and priority to U.S. Provisional Application Ser. No. 61/697,671, filed on Sep. 6, 2012. The entire contents of each of the foregoing applications are hereby incorporated herein by reference.

BACKGROUND

Technical Field

The present disclosure relates to medical devices having components to treat tissue with light energy. More particularly, the present disclosure relates to open or endoscopic surgical forceps that incorporate optics to create conditions of frustrated total internal reflection to facilitate energy-efficient sealing and cutting of tissue using light energy.

Description of Related Art

In many surgical procedures, body vessels, e.g., blood vessels, ducts, adhesions, fallopian tubes, or the like are sealed to defunctionalize or close the vessels. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal by heating tissue have been employed.

Endoscopic or open forceps are particularly useful for sealing since forceps utilize mechanical action to constrict, grasp, dissect and/or clamp tissue. Current vessel sealing procedures utilize radio frequency treatment to heat and desiccate tissue causing closure and sealing of vessels or tissue.

SUMMARY

As used herein, the term "distal" refers to that portion that is further from an operator while the term "proximal" refers to that portion that is closer to an operator. As used herein, the term "treat" refers to performing a surgical treatment to tissue including, but not limited to heating, sealing, cutting, sensing, and/or monitoring.

As used herein, the term "light source" broadly refers to all types of devices or elements that generate or transmit light for medical use (e.g., tissue treatment). These devices include lasers, light emitting diodes (LEDs), lamps, and other devices that generate light having a wavelength that is within the light spectrum (e.g., from infrared light to ultraviolet light). Also, the light sources described herein may be used interchangeably. For example, an LED light source may be used interchangeably with a laser light source.

Light sources may produce laser light having a wavelength from about 200 nm to about 15,000 nm and include but are not limited to ruby lasers, tunable titanium-sapphire lasers, copper vapor lasers, carbon dioxide lasers, alexandrite lasers, argon lasers such as argon fluoride (ArF) excimer lasers, argon-dye lasers, potassium titanyl phosphate (KTP) lasers, krypton lasers such as krypton fluoride (KrF) excimer lasers, neodymium:yttrium-aluminum-garnet (Nd:YAG) lasers, holmium:yttrium-aluminum-garnet (Ho:YAG) lasers, erbium:yttrium-aluminum-garnet (Er:YAG) lasers, diode lasers, fiber lasers, xenon chloride (XeCl) excimer lasers, tubanle thalium lasers, and any combinations of these lasers. Additional types of light sources include fiber optic light sources and deuterium light sources.

In some embodiments, a light source may generate light of multiple wavelengths. For example, Nd:YAG and KTP laser light may be generated by a single laser source. Nd:YAG laser light, which has a large optical depth or thickness, may be used for sealing and KTP laser light, which has a small optical depth or thickness, may be used for cutting or for sealing small vessels or thin tissue.

As described in more detail below with reference to the accompanying figures, the present disclosure relates to open or endoscopic surgical forceps that incorporate optics to create conditions of frustrated total internal reflection to facilitate energy-efficient sealing and cutting of tissue using light energy. In some embodiments, one or both jaw member of the surgical forceps is optically designed so that light of a therapeutic wavelength, e.g., infrared laser light having a wavelength between 800 nm and 1550 nm, is totally internally reflected from the boundary between a tissue-contacting surface of one or both jaw members and air, when tissue is not grasped by the surgical forceps. This creates an evanescent wave on the tissue-contacting surface of one or both jaw members.

When tissue is grasped by the surgical forceps, the tissue-contacting surface of one or both jaw members comes into contact with the tissue and the evanescent wave allows light energy to be transmitted to the tissue only through those portions of the tissue-contacting surface that are in contact with the tissue. The light energy is absorbed by the tissue resulting in heat that is used to fuse tissue (e.g., sealing) and/or separate tissue (e.g., cutting). As a result, light energy is efficiently delivered to the tissue because there is a decreased amount of wasted or lost light energy.

In some embodiments, the surgical devices sense and/or monitor the tissue during a surgical procedure to determine when a seal cycle is complete, to determine the efficacy of a tissue seal and/or to measure jaw pressure. In some embodiments, tissue separation may be accomplished with the same light energy device used for tissue sealing, thereby eliminating the need for a separate mechanical blade that is traditionally used for tissue separation in jaw members.

In aspects, the present disclosure features a medical instrument. The medical instrument includes a first jaw member having a tissue-contacting surface and a second jaw member movably coupled to the first jaw member. The first jaw member and the second jaw member cooperate to grasp tissue between the first jaw member and the second jaw member. The medical instrument further includes a light source that provides a light beam for sealing tissue. The light source is optically coupled to the first jaw member so that the light beam is internally reflected from the interface between the tissue-contacting surface of the first jaw member and air when tissue is not grasped between the first jaw member and the second jaw member. The light source is also optically coupled to the tissue-contacting surface of the first jaw member so that at least a portion of the light beam is transmitted through that portion of the tissue-contacting surface of the first jaw member that is in contact with the tissue when the tissue is grasped between the first jaw member and the second jaw member.

The light source of the medical instrument may include an optical fiber, a light-emitting diode, a laser, a diode laser, a fiber laser, or any combination of these light sources. The light source may be configured to rotate and/or translate with respect to the first jaw member. The light source may also be configured to scan the tissue with the light beam.

The second jaw member of the medical instrument may include a light-absorbent material that absorbs light that is transmitted through the tissue. Alternatively, the second jaw member may include a light-reflective material that reflects light that is transmitted through the tissue. The light-absorbent material or the light-reflective material may be coated onto the surface of the second jaw member.

The light source may be movable and may be configured to move to a position based on at least one optical property of the tissue while the tissue is in contact with at least a portion of the tissue-contacting surface of the first jaw member. The at least one optical property of the tissue may include index of refraction, absorption coefficient, scattering coefficient, anisotropy coefficient, or any combination of these optical properties. The light source may be rotatable to selectively provide a light beam having a variable angle of incidence with respect to an axis normal to the tissue-contacting surface of the first jaw member.

The medical instrument may further include an optical element disposed in the first jaw member and having a side that forms at least a portion of the tissue-contacting surface of the first jaw member. The optical element may be a light guide that extends along at least a portion of a longitudinal axis of the first jaw member. A light-absorbent element or a light-reflective element may be coupled to at least a portion of a distal end of the light guide. The optical element may be a crystal configured to circulate the light provided by the light source when tissue is not grasped between the first jaw member and the second jaw member.

The optical element may include a plurality of crystals and the light source may include a plurality of light sources coupled to the plurality of crystals, respectively. Each of the plurality of light sources may be configured to provide a light beam having a different wavelength.

The optical element may be formed of a material including sapphire, ruby, YAG, alexandrite, flint, BK7 glass, fused silica, or any combination of these materials.

The second jaw member of the medical instrument may include a second optical element having a side that forms at least a portion of a second tissue-contacting surface. The medical instrument may further include a second light source that provides a second light beam for sealing tissue. The second light source is optically coupled to the second optical element so that the second light beam is totally internally reflected from the interface between the second tissue-contacting surface of the second optical element and air when tissue is not grasped between the first jaw member and the second jaw member. The second light source may also be optically coupled to the second optical element so that at least a portion of the second light beam is transmitted through that portion of the second tissue-contacting surface of the second optical element that is in contact with the tissue when the tissue is grasped between the first jaw member and the second jaw member.

The first jaw member of the medical instrument may be hollow and the optical element may be disposed within the first jaw member. Alternatively, the optical element may form at least a portion of the first jaw member.

In yet other aspects, the present disclosure features an optical-based tissue-sealing system. The optical-based tissue-sealing system includes a housing and an end effector assembly operably connected to the housing. The end effector assembly includes a first jaw member having a tissue-contacting surface. The end effector assembly also includes a second jaw member movably coupled to the first jaw member. The first jaw member and the second jaw member cooperate to grasp tissue between the first jaw member and the second jaw member.

The optical-based tissue-sealing system also includes a light source that provides a light beam for sealing tissue. The light source is optically coupled to the tissue-contacting surface so that the light beam is totally internally reflected from an interface between the tissue-contacting surface of the first jaw member and air when tissue is not grasped between the first jaw member and the second jaw member. The light source is also optically coupled to the first jaw member so that at least a portion of the light beam is transmitted through the tissue-contacting surface of the first jaw member to the tissue when tissue is grasped between the first jaw member and the second jaw member. The optical-based tissue-sealing system further includes a controller coupled to the light source. The controller controls at least one parameter of the light beam. The one or more parameters of the light beam may include intensity, wavelength, polarization, angle of incidence with respect to an axis normal to the tissue-contacting surface of the first jaw member, or any combination of these parameters.

The optical-based tissue-sealing system may further include a sensor that senses at least one optical property of the tissue and the controller may further control at least one parameter of the light beam based upon the at least one optical property of the tissue.

In yet other aspects, the present disclosure features a method of treating tissue with an optical energy-based medical instrument. The method includes directing a light beam into at least one optical element of a first jaw member of an optical energy-based instrument with a light beam, reflecting the light beam within the optical element from an interface between a surface of the optical element and a media having a low index of refraction, grasping tissue between the first jaw member and a second jaw member of an optical energy-based medical instrument, and transmitting at least a portion of the light beam through a tissue-contacting surface of the optical element to the tissue when the tissue is grasped between the first jaw member and the second jaw member.

BRIEF DESCRIPTION OF THE DRAWINGS

Various embodiments of the medical systems, devices, instruments, and methods are described herein with reference to the drawings wherein.

DETAILED DESCRIPTION

Figure 1A:
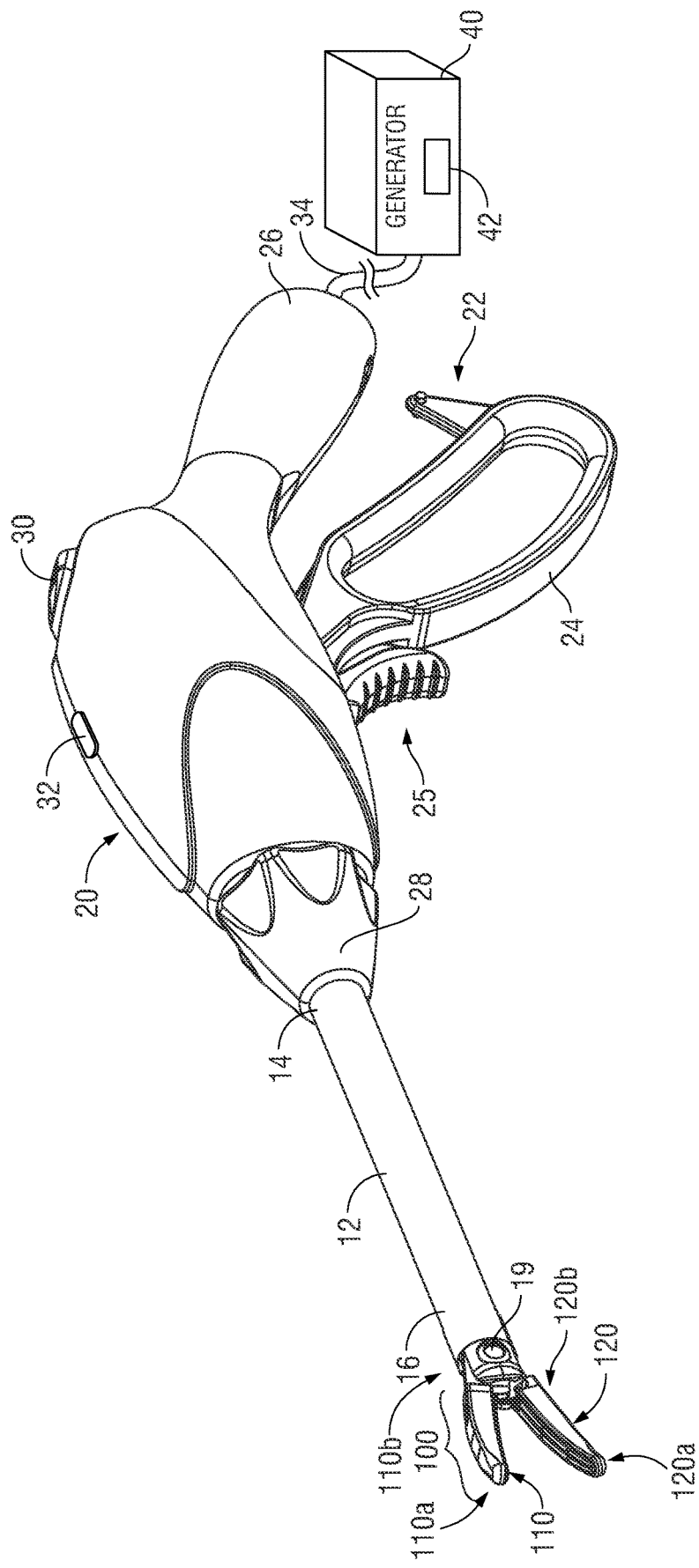
FIG. 1A is a perspective view of an optical-based surgical system including a surgical instrument having an end effector assembly that incorporates optical components for creating conditions of frustrated total internal reflection within one or more jaw members of the end effector assembly according to embodiments of the present disclosure.

Embodiments of the presently-disclosed surgical instrument are described in detail with reference to the drawings wherein like reference numerals identify similar or identical elements.

FIG. 1A shows an endoscopic surgery forceps 10 that may be used with any of the embodiments of end effector assemblies described below. In FIG. 1A, forceps 10 is coupled to a light energy source (e.g., a generator 40) for generating light energy adapted to seal tissue. Light energy source (e.g., generator 40) is configured to output light energy having a wavelength from about 200 nm to about 11,000 nm. Forceps 10 is coupled to the generator 40 via a cable 34 that includes one or more optical fibers to transmit light energy and one or more electrical conductors to transmit control signals between the forceps 10 and the generator 40. The generator 40 may produce light energy having one or more wavelengths. In some embodiments, Nd:Yag and KTP laser light may be produced by the same laser source. Various embodiments of the forceps 10 using the light energy are described below.

Forceps 10 is configured to support an end effector assembly (e.g., end effector assembly 100) at a distal end thereof. Forceps 10 includes various conventional features (e.g., a housing 20, a handle assembly 22, a trigger assembly 25, and a rotating assembly 28) that enable forceps 10 and end effector assembly 100 to mutually cooperate to grasp, seal, divide and/or sense tissue. Forceps 10 generally includes housing 20 and handle assembly 22 that includes movable handle 24 and a handle 26 that is integral with housing 20. The handle 24 is movable relative to the handle 26 to actuate end effector assembly 100 via a drive assembly (not shown) to grasp tissue.

In some embodiments, trigger assembly 25 may be configured to actuate a knife blade (not shown) or another component. Forceps 10 also includes shaft 12 having a distal portion 16 that mechanically engages end effector assembly 100 and a proximal portion 14 that mechanically engages housing 20 proximate rotating assembly 28 disposed on housing 20. Rotating assembly 28 is mechanically associated with shaft 12 such that rotational movement of rotating assembly 28 imparts similar rotational movement to shaft 12 that, in turn, rotates end effector assembly 100.

End effector assembly 100 includes two jaw members 110 and 120, each having proximal ends 110a, 120a and distal ends 110b, 120b, respectively (see FIG. 1A). One or both jaw members 110 and 120 are pivotable about a pin 19 and one or both are movable from a first position wherein jaw members 110 and 120 are spaced relative to another, to a second position wherein jaw members 110 and 120 are closed and cooperate to grasp tissue between the jaw members 110 and 120.

Figure 2A:
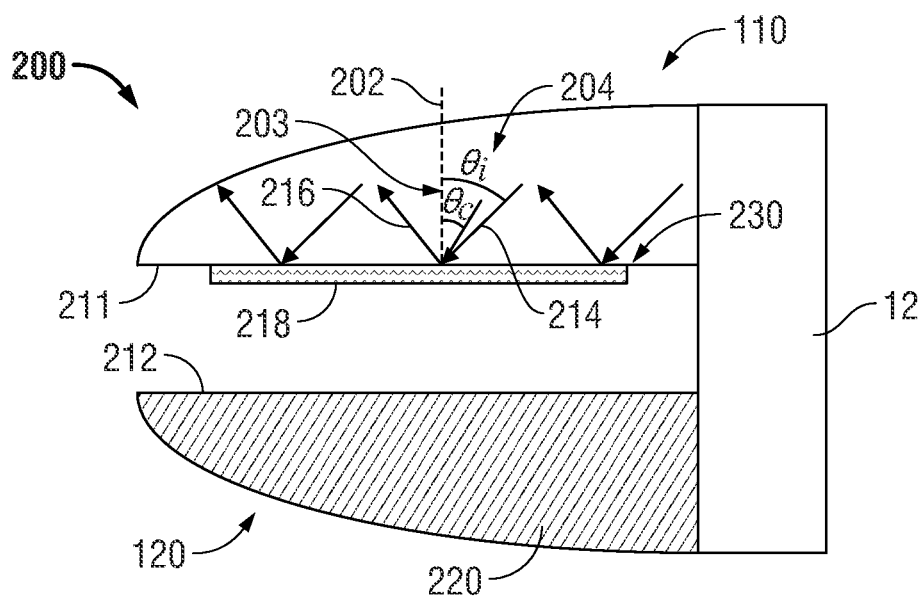
FIGS. 2A and 2B are schematic side, cross-sectional views of an end effector assembly according to embodiments of the present disclosure.

Each jaw member 110 and 120 includes a tissue contacting surface 211 and 212, respectively, disposed on an inner-facing surface thereof (see FIG. 2A). Tissue-contacting surfaces 211, 212 cooperate to grasp and seal tissue held between the tissue-contacting surfaces. Tissue-contacting surfaces 211, 212 are connected to generator 40 that can transmit light energy through the tissue held between the tissue-contacting surfaces 211, 212.

First and second switch assemblies 30 and 32 are configured to selectively provide light energy to end effector assembly 100. More particularly, the first switch assembly 30 may be configured to perform a first type of surgical procedure (e.g., seal, cut, and/or sense) and a second switch assembly 32 may be configured to perform a second type of surgical procedure (e.g., seal, cut, and/or sense). It should be noted that the presently-disclosed embodiments may include any number of suitable switch assemblies and are not limited to only switch assemblies 30 and 32. It should further be noted that the presently-disclosed embodiments may be configured to perform any suitable surgical procedure and are not limited to only sealing, cutting and sensing.

The housing 20 further includes one or more light-transmissive elements, such as one or more optical fibers disposed within a cable 34 that connects the forceps 10 to the generator 40. The cable 34 may include a plurality of optical fibers (not shown) that are configured to transmit light energy through various paths and ultimately to end effector assembly 100 and one or more optical elements that are configured to create conditions of total internal reflection at one or both of the tissue contacting surfaces 211 and 212.

First and second switch assemblies 30 and 32 may also cooperate with a controller 42, which may be implemented by a logic circuit, a computer, a processor, and/or a field programmable gate array. The controller 42 may automatically trigger one of the switches to change between a first mode (e.g., sealing mode) and a second mode (e.g., cutting mode) upon the detection of one or more parameters, properties, or thresholds. In some embodiments, the controller 42 is also configured to receive various sensor feedback and to control the generator 40 based on the sensor feedback. The embodiments of the present disclosure allow the jaw members 110 and 120 to seal and/or cut tissue using light energy.

In some embodiments, the controller 42 may include a feedback loop that indicates when a tissue seal is complete based upon one or more of the following parameters or properties: tissue temperature, change in impedance of the tissue over time, change in optical characteristics of tissue (opaqueness, clarity, etc.), rate of change of these properties, and combinations thereof. An audible or visual feedback monitor may be employed to convey information to the surgeon regarding the overall seal quality or the completion of an effective tissue seal.

Figure 1B:
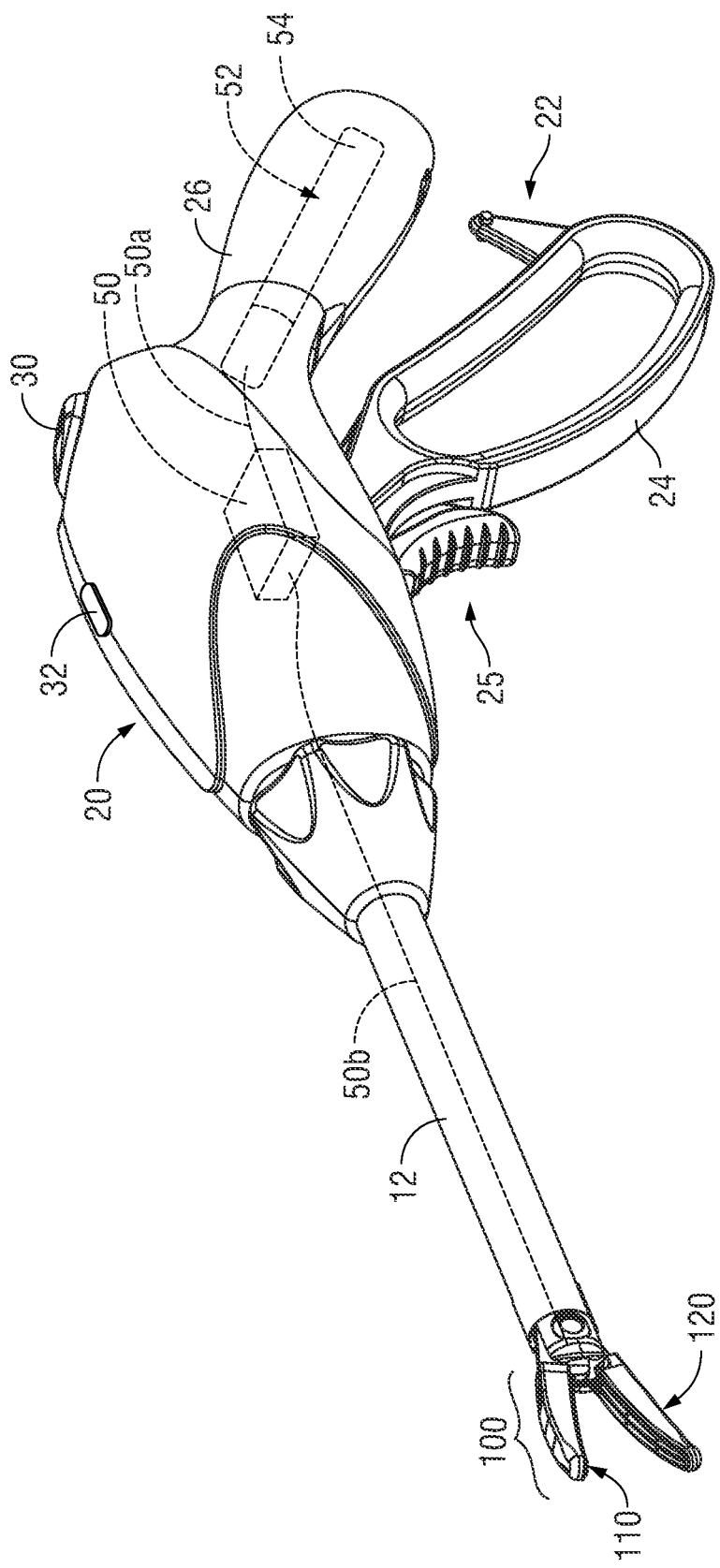
FIG. 1B is a perspective view of a cordless, optical-based surgical instrument having an end effector assembly that incorporates optical components for creating conditions of frustrated total internal reflection within one or more jaw members of the end effector assembly according to embodiments of the present disclosure.

Referring now to FIG. 1B, forceps 10 is shown having a portable configuration and includes an internal energy source 50 for generating light energy that is operably coupled to a battery compartment 52 via one or more wires 50a. In some embodiments, one or more battery-operated laser diodes or fiber lasers may also be used to provide a portable light energy source. Internal energy source 50 may be configured to provide light energy to the end effector assembly 100 and optical elements via one or more laser fibers 50b or any other suitable transmission medium. Battery compartment 52 may be configured to receive one or more batteries 54 for providing suitable energy to internal energy source 50. In embodiments, the controller 42 may also be disposed within the forceps 10 (e.g., housing).

Battery compartment 52 may be defined within any suitable portion of housing 20 of forceps 10, such as the fixed handle 26, as shown in FIG. 1B. Suitable batteries may include, but are not limited to a nickel-cadmium, lithium-ion, rechargeable, or any other suitable type. The location of internal energy source 50 provides an operator increased maneuverability and convenience when performing a surgical treatment with forceps 10.

FIG. 2A illustrates an end effector assembly 200 according to the present disclosure, which is configured for use with instrument 10 of FIG. 1A, instrument 11 of FIG. 1B, or any other suitable surgical instrument. The end effector assembly 200 includes jaw members 110 and 120 having proximal ends 110a, 120a and distal ends 110b, 120b. The first jaw member 110 (e.g., a top jaw member) has a first tissue-contacting surface 211 and the second jaw member 120 (e.g., a bottom jaw member) has a second tissue-contacting surface 212. The first jaw member 110 and the second jaw member 120 are movable with respect to each other so that tissue can be grasped between the first tissue-contacting surface 211 and the second tissue-contacting surface 212.

According to the various embodiments of the present disclosure, incident light beam 214 is directed at the tissue-contacting surface 211 of the first jaw member 110 from within the first jaw member 110. The incident light beam 214 is directed at a predetermined angle $\theta_i$ with respect to the axis 202 perpendicular to the tissue-contacting surface 211 of the first jaw member 110 so that the incident light beam 214 are totally reflected as reflected light beams 217 at the interface between the tissue-contacting surface 211 and the air 205, e.g., when the tissue-contacting surface 211 is not in contact with tissue. The tissue-contacting surface 211 may be made of a material, e.g., coated with a material, that enables total reflection of the incident light beam 214 when the tissue-contacting surface 211 is not in contact with tissue.

Refraction and reflection at a planar boundary or interface between two media of different refractive indices is described by Snell's law and Fresnel's equations, which are related to Maxwell's wave equations for electromagnetic radiation at a boundary or interface. As shown in FIG. 2A, for refraction from the tissue-contacting surface 211 of the first jaw member 110 with refractive index $n_2$, to air 205 with lower refractive index $n_1$, Snell's law provides the following relationship:

$$n_2 \sin \theta_i = n_1 \sin \theta_r$$

where $\theta_i$ is the angle of incidence and $\theta_r$ is the angle of refraction.

Total internal reflection occurs at the interface or boundary 230 defined by the first tissue-contacting surface 211 and the air 205 when the angle of incidence $\theta_i$ (204) is greater than or equal to a critical angle $\theta_c$ (203), which is defined by the following equation:

$$\theta_c = \arcsin(n_2/n_1).$$

This reflection is "total" because a certain amount of energy is present in the air 205 in a thin layer adjacent to the boundary 230. As shown in FIG. 2A, this energy is in the form of evanescent waves 218. The waves in this layer are called evanescent waves because they decay rapidly to zero.

When tissue 213 is not in contact with the tissue-contacting surface 211 of the first jaw member 110, the reflected light beams 214 are contained within the first jaw member 110 so that they are not transmitted outside of the first jaw member 110. In some embodiments, the inner or outer surfaces of the first jaw member 110 are coated with a light-reflective or a light-absorbent material to prevent the totally reflected light beam 216 from being transmitted outside of the first jaw member 110.

Figure 2B:
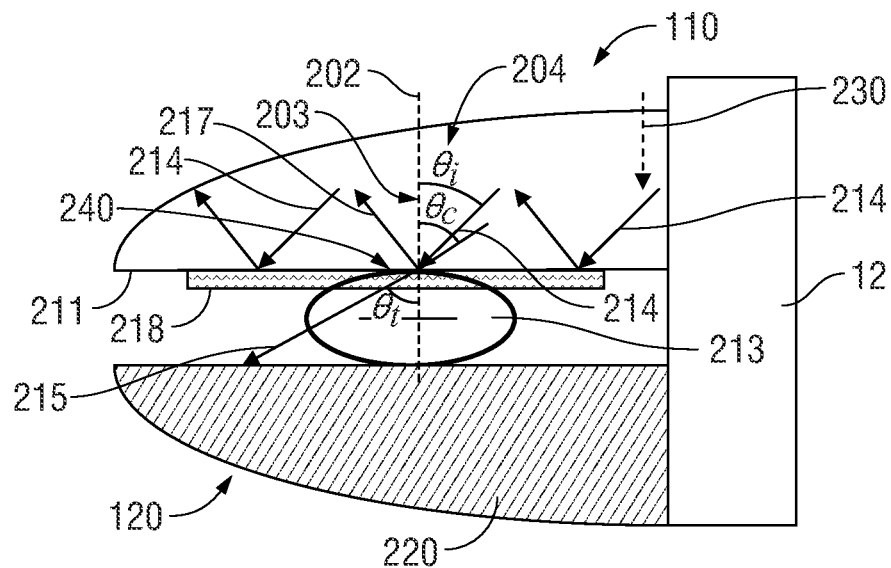

As shown in FIG. 2B, when tissue 213 is grasped between the first tissue-contacting surface 211 and the second tissue-contacting surface 212, the tissue 213 comes into contact with the first tissue-contacting surface 211, thus forming a new interface 240 between the first tissue-contacting surface 211 and the tissue 213. Because the index of refraction of tissue 213 (e.g., 1.5) is much greater than the index of refraction of air (e.g., 1.0), the total internal reflection is "frustrated" and the evanescent wave 218 transfers light energy from the light beam 214 to the tissue 213.

In other words, a new critical angle 203 is defined by the following equation:

$$\theta_c = \arcsin(n_2/n_3),$$

where $n_2$ is the index of refraction of the tissue-contacting surface 211 of the first jaw member 110 and $n_3$ is the index of refraction of the tissue 213. This new critical angle 203 is greater than the angle of incidence of the light beam 214. As a result, a transmitted portion 215 of the light beam 214 is transmitted to the tissue 213 and the remaining reflected portion 217 of the light beam 214 is reflected from the new interface between the first tissue-contacting surface 211 and the tissue 213.

Thus, as illustrated in FIGS. 2A and 2B, the incident light beam 214 passes through that portion of the tissue-contacting surface 211 that is in contact with tissue 213. Otherwise, the incident light beam 214 is totally internally reflected. As a result, the medical device of FIGS. 2A and 2B saves power because light energy is transmitted to the tissue 213 only when it comes into contact with the tissue-contacting surface 211.

Figure 3A:
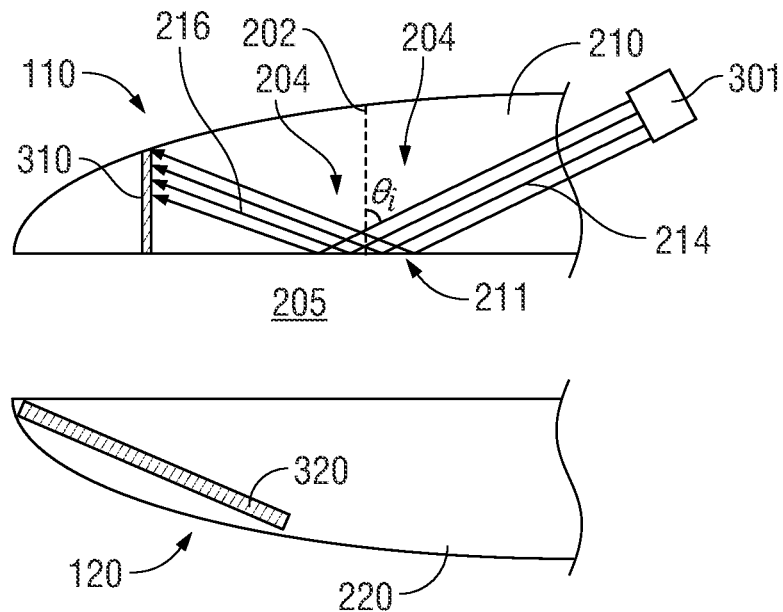
FIGS. 3A and 3B are schematic side, cross-sectional views of jaw members according to embodiments of the present disclosure.

FIG. 3A illustrates an embodiment of a first jaw member 120 that is optically coupled to a light source 301. The light source 301 may be an optical assembly that includes an LED (not shown) that generates light and a beam-forming optical element (not shown) that forms the light into a beam. Alternatively, the light source 301 is a light guide that carries light from an LED (not shown) to the first jaw member 110.

The light source 301 directs an incident light beam 214 at the tissue contacting surface 211 of the first jaw member 110. The light source 301 is positioned to direct the incident light beam 214 at a desired incident angle 204 with respect to the axis 202 normal to the tissue-contacting surface 211 of the first jaw member 110. As described above, the incident angle 204 is selected so that it is greater than the critical angle to facilitate total internal reflection when air 205 is in contact with the tissue-contacting surface 211 of the first jaw member 110.

The reflected light beam 216 is absorbed by a light-absorbent optical element 310 so that the reflected light beam 216 is not transmitted outside of the first jaw member 110. In other embodiments, the light-absorbent optical element 310 is replaced with a light-reflective optical element, which may reflect the reflected light beam 216 back to the tissue-contacting surface 211 of the first jaw member 110 or to an optical element that carries the reflected light beam 216 away from the first jaw member 110. The light-absorbent optical element 310 may be formed of a material that dissipates heat generated.

Figure 3B:
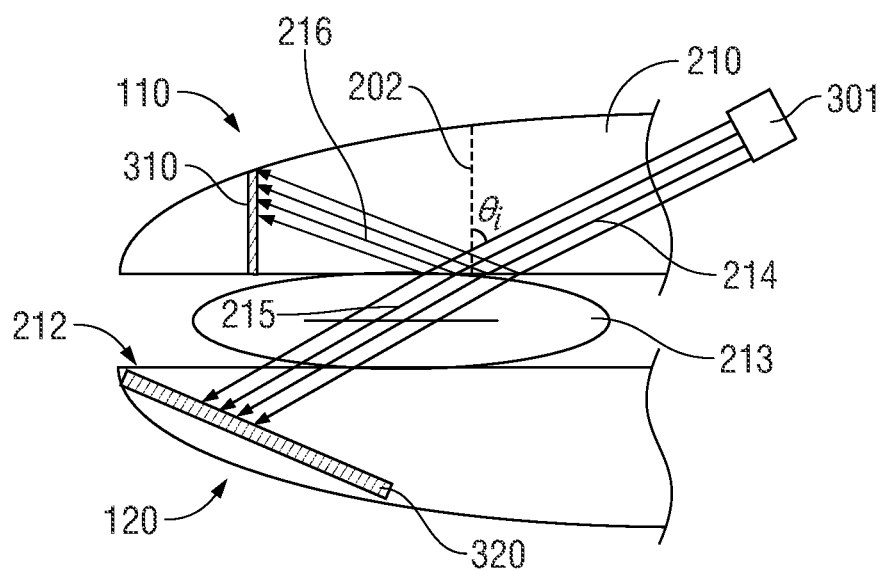

As illustrated in FIG. 3B, when the first jaw member 110 and the second jaw member 120 grasp the tissue 213, at least a portion of the light beam 214, i.e., the transmitted portion 215, is transmitted to the tissue 213. The transmitted portion 215 of the light beam 214 that passes through the tissue 213 is absorbed and/or reflected by optical element 320 disposed in the second jaw member 120.

If the optical element 320 is light-reflective, it may be positioned at an angle with respect to the tissue-contacting surface 212 of the second jaw member 120 so that the transmitted portion 215 of the incident light beam 214 that passes through the tissue 213 is reflected back to the tissue 213.

Figure 4A:
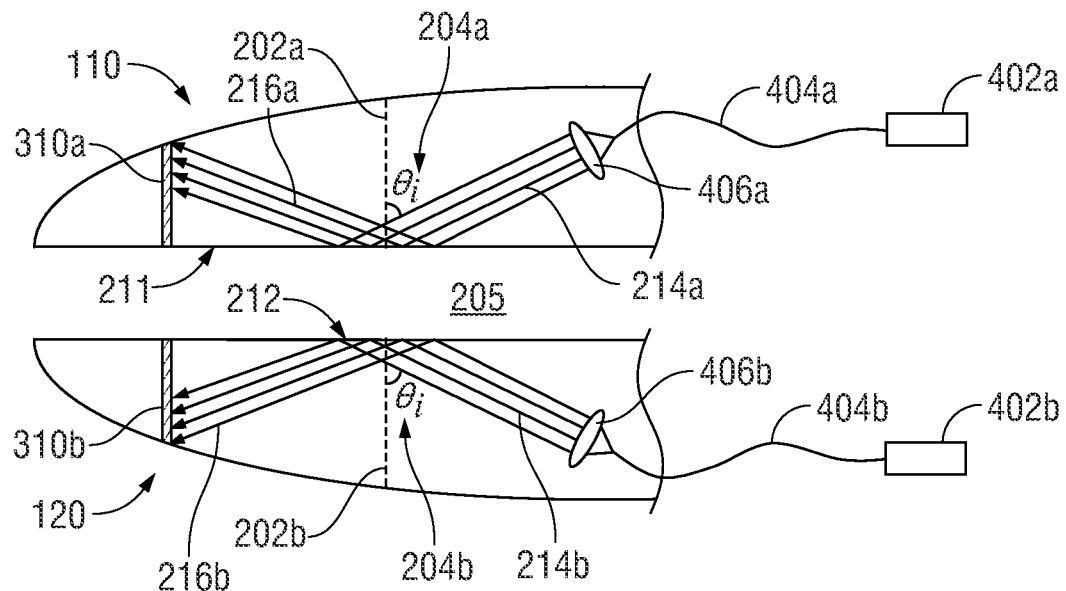
FIGS. 4A and 4B are schematic side, cross-sectional views of jaw members incorporating fiber optic components in both jaw members according to embodiments of the present disclosure.
Figure 4B:
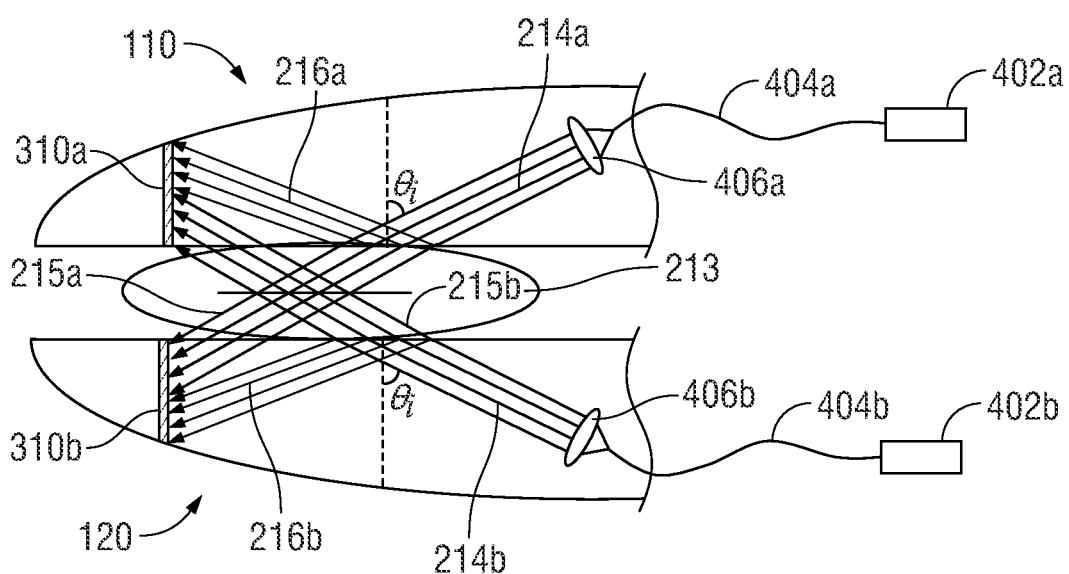

FIGS. 4A and 4B illustrate an end effector assembly that incorporates fiber optic components 402*a*, 404*a*, 406*a*, 402*b*, 404*b*, and 406*b*. As shown, the fiber optic components 404*a*, 406*a* disposed in the first jaw member 110 are the same as the fiber optic components 404*b*, 406*b* disposed in the second jaw member 120. The first jaw member 110 includes a first lens 406*a* that is optically coupled to a first light source 301*a* via an optical fiber 404*a*. In this configuration, the first light source 301*a* is not disposed within the jaw members 110, 120. The first light source 301*a*, however, may be disposed elsewhere in the forceps 10, the forceps 11, the generator 40, or the internal energy source 50. For example, the first light source 301*a* may be disposed within the handle 26, the housing 20, or the shaft 12 of the forceps 10.

The first light source 301*a* generates an optical signal that is transmitted to the first lens 406*a* via the optical fiber 404*a*. The first lens forms a first light beam 214*a* and directs the first light beam 214*a* towards the first tissue-contacting surface 211 of the first jaw member 110 at a first incident angle 204*a* with respect to an axis 202*a* normal to the first tissue-contacting surface 211. The first incident angle 204*a* is selected so that the first light beam 214*a* is totally reflected 216*a* from the first tissue-contacting surface 211 when tissue does not contact the first tissue-contacting surface 211. The first jaw member 110 also includes a light-absorbent optical element 310*a* that absorbs the reflected light beam 216*a*. In other embodiments, the light-absorbent optical element 310*a* may be replaced with a light-reflective optical element.

Like the first jaw member 110, the second jaw member 120 includes a second lens 406*b* optically coupled to a second light source 301*b* via an optical fiber 404*a*. The second light source 301*b* (which may be a different type of light source than first light source 301*a* or the same) generates an optical signal that is transmitted to the second lens 406*b* via the optical fiber 404*a*. The second lens 406*b* forms a second light beam 214*b* and directs the second light beam 214*b* towards the second tissue-contacting surface 211 of the second jaw member 120 at a second incident angle 204*b* with respect to an axis 202*b* normal to the second tissue-contacting surface 212. The second incident angle 204*b* is selected so that the second light beam 214*b* is totally reflected from the second tissue-contacting surface 212 when tissue does not contact the second tissue-contacting surface 212. The second jaw member 120 also includes a light-absorbent optical element 310*b* that absorbs the reflected light beam 216*b*. In other embodiments, the light-absorbent optical element 310*b* may be replaced with a light-reflective optical element.

As shown in FIG. 4B, when tissue 213 is grasped between the first jaw member 110 and the second jaw member 120, a portion of the first light beam 214*a* is transmitted as light beam 215*a* to the tissue and a portion of the second light beam 214*b* is transmitted as light beam 215*b* to the tissue 213. In this manner, light can be applied to both sides of the tissue 213 to seal the tissue 213 more quickly and evenly. The transmitted light beam 215*a* is then absorbed by the light-absorbent optical element 310*b* and the transmitted light beam 215*b* is absorbed by the light-absorbent optical element 310*a*.

In an alternative embodiment, the light sources 402*a*, 402*b* may be replaced by a single light source that emits a light beam that is split and transmitted via two different fibers to the jaw members 110, 120, respectively. For example, a light source may emit a light beam that is split and transmitted via fibers 404*a* and 404*b* to the jaw members 110, 120, respectively.

Figure 5A:
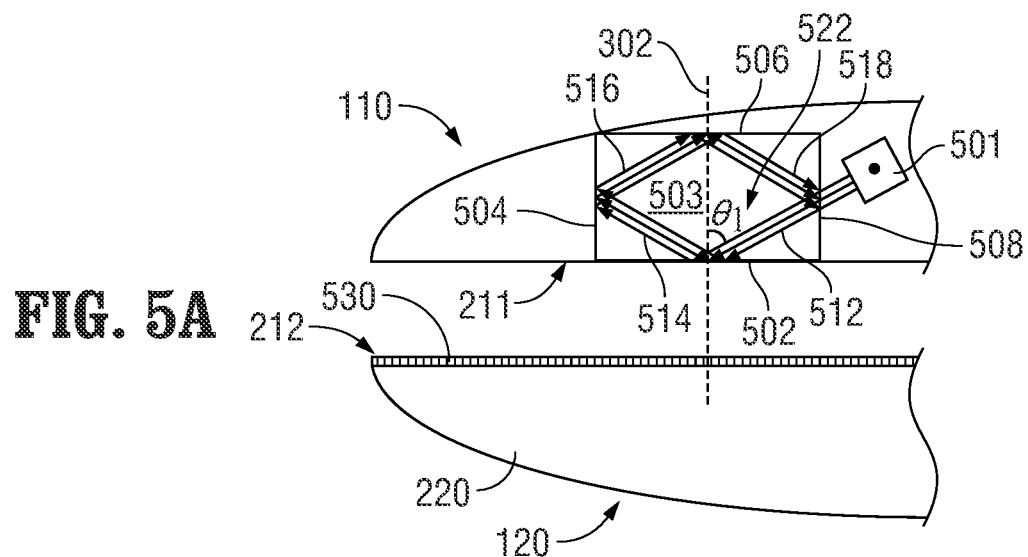
FIGS. 5A-5C are schematic side, cross-sectional views of jaw members, one of which includes an optical element and a movable light source, according to embodiments of the present disclosure.
Figure 5B:
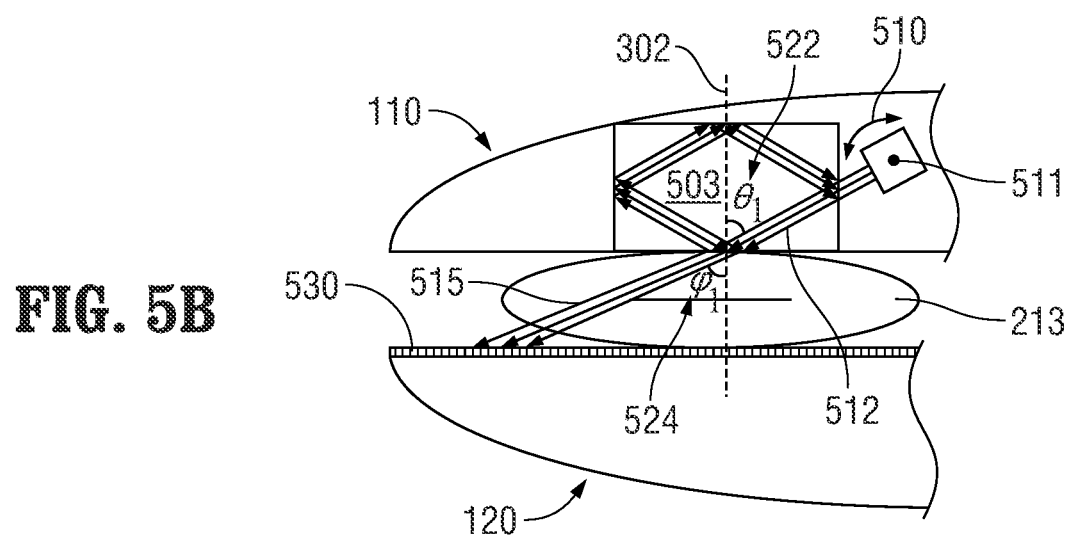
Figure 5C:
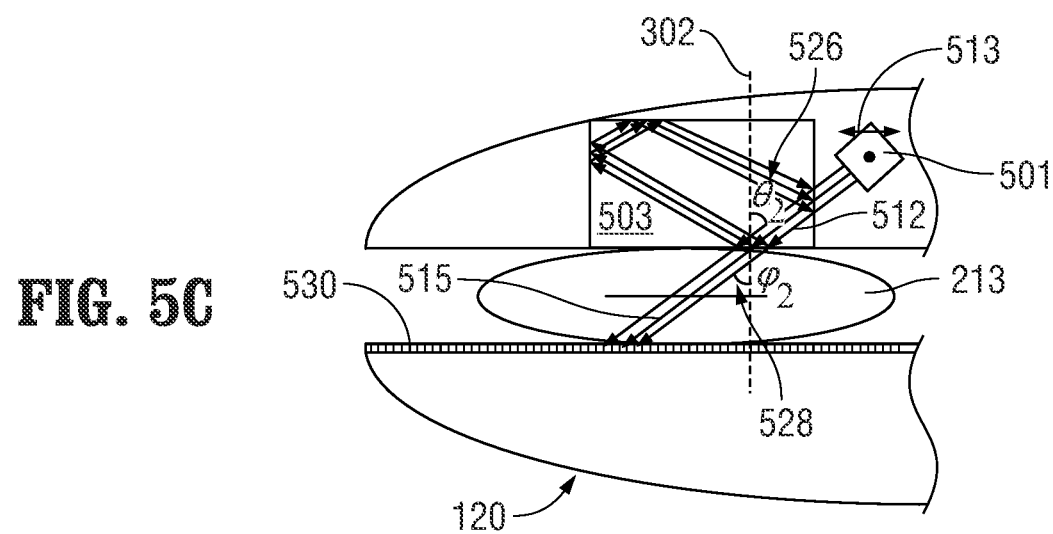

FIGS. 5A-5C illustrate another embodiment that incorporates a movable light source 501 and a crystal 503, e.g., a prism or other crystal structure. As shown in FIG. 5A, the first jaw member 110 includes the crystal 503 having four surfaces: a first crystal surface 502, a second crystal surface 504, a third crystal surface 506, and a fourth crystal surface 508. The first crystal surface 502 forms a portion of the tissue-contacting surface 211 of the first jaw member 110. The movable light source 501 is positioned to direct a light beam 512 at a first incident angle 522 with respect to an axis 302 normal to the first crystal surface 502. The first incident angle 522 is selected so that the light beam 512 reflects from the first surface 502 as reflected light beam 514 when tissue is not in contact with the first surface 502.

The first jaw member 110, the light source 501, and the crystal 503 are configured so that the light beam 512 also reflects off of the second crystal surface 504 as reflected light beam 516, the third crystal surface 506 as reflected light beam 518, and the fourth crystal surface 508. Specifically, the first jaw member 110 may be a hollow structure that is filled with air 210 and the crystal 503 has an index of refraction much greater than the air 210. As a result, total internal reflection can be achieved within the crystal 503 over a range of angles that are greater than the critical angle. The crystal 503 is also configured so that the incident angle of the light beam 512 with respect to the axis 302 normal to the second crystal surface 504, the third crystal surface 506, and the fourth crystal surface 508 is greater than the critical angle. The movable light source 501 is positioned to create an incident angle with respect to the axes (e.g., axis 302) normal to the crystal surfaces 502, 504, 506, 508 that is greater than the critical angle.

As shown in FIG. 5A, the tissue-contacting surface 212 of the second jaw member 120 is coated with a light-absorbent optical material 530. In some embodiments, the light-absorbent optical material 530 is a material that increases in temperature when it is illuminated with light.

Referring now to FIG. 5B, when tissue 213 is grasped between the first jaw member 110 and the second jaw member 120, conditions of frustrated total internal reflection are created and the light beam 512 is transmitted through the tissue 213 to the light-absorbent optical material 530. As shown, the angle 524 of the transmitted light beam 515 with respect to the axis 302, which is perpendicular to the tissue-contacting surface 211 of the first jaw member 110, is greater than the incident angle 522 according to Snell's law. As a result, the transmitted light beam 515 passes through a portion of the tissue 213 at an angle 528 with respect to the axis 302.

As shown in FIG. 5C, the movable light source 501 is rotatable about a pivot point 511 and translatable. As a result, the light beam 515 can be rotated counter-clockwise or clockwise 510, or translated right or left 513, to direct the transmitted light beam 515 through different portions of the tissue 213. In this way, the transmitted light beam 515 can be scanned through multiple portions of the tissue 213. When the movable light source 501 is rotated about the pivot point 511 of the first jaw member 110, the incident angle also changes to a second incident angle 526. This process may allow larger tissue structures to be treated with smaller light sources, may produce varying or different surgical tissue effects (sealing versus cutting), and may provide more reliable and stronger seals.

In embodiments, the light source may be translatable to enable scanning of multiple portions of the tissue 213. The light source may also be rotatable to enable changing of the incident angle with respect to the tissue-contacting surface of the optical element 503.

In alternative embodiments, the movable light source 501 may be replaced by a single fixed light source that transmits light to the jaw members 110, 120 via a movable crystal or lens, which moves, e.g., rotates, to scan the light beam 512 over multiple portions of the tissue 213.

Figure 6A:
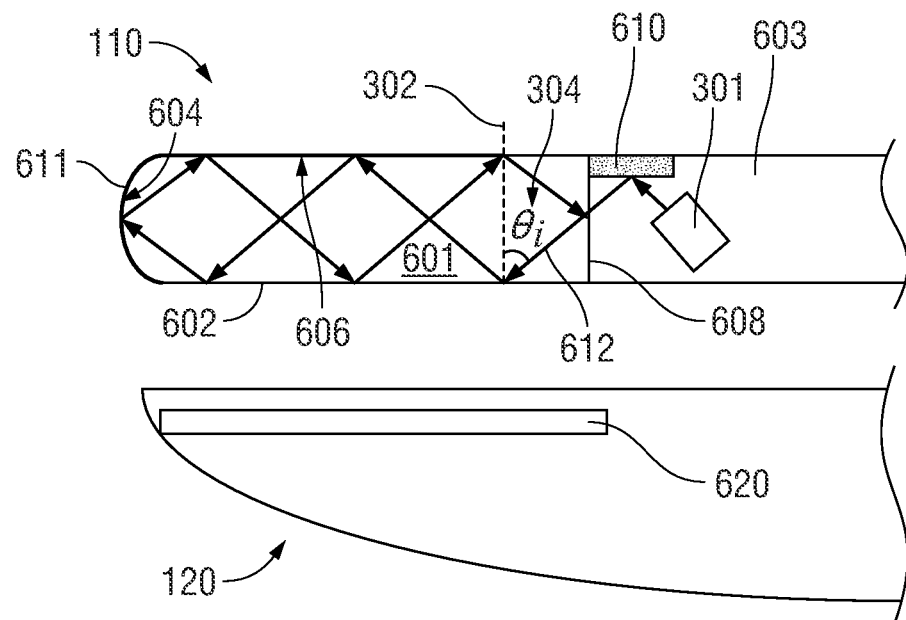
FIGS. 6A-6B are schematic side, cross-sectional views of jaw members including an optical element that forms a portion of a jaw member according to embodiments of the present disclosure.
Figure 6B:
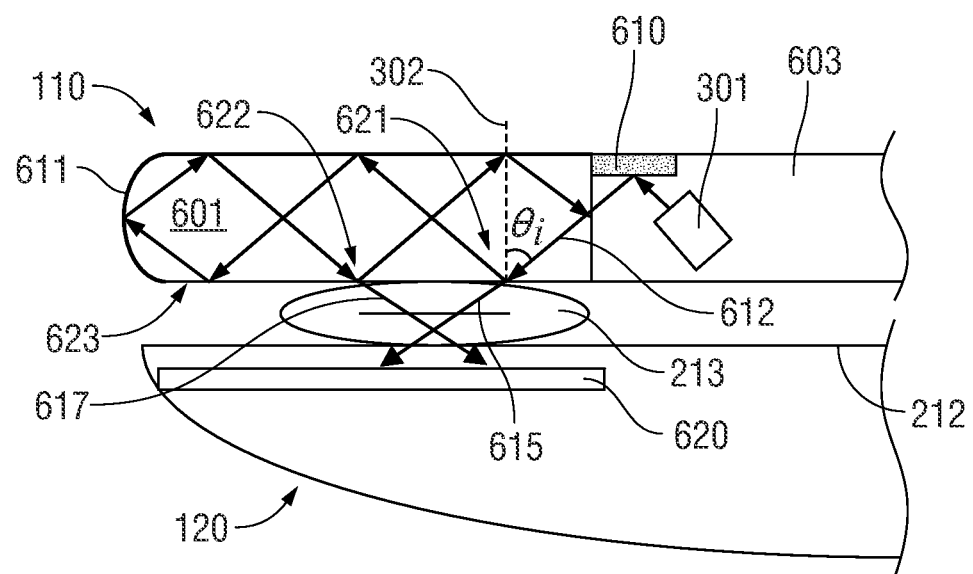

FIGS. 6A and 6B illustrate an embodiment in which a portion of the first jaw member 110 is a crystal structure. As shown in FIG. 6A, the first jaw member 110 includes a crystal portion 601 and a non-crystal portion 603. The non-crystal portion 603 contains the light source 301 and a reflective optical element 610, e.g., a mirror, which reflects light generated by the light source 301 into the crystal portion 601. The light source 301 is positioned so that the incident angle 304 of the light beam 612 with respect to the axis 302 is greater than the critical angle. Thus, when tissue is not in contact with the first jaw member 110, the light beam 612 is totally internally reflected from the first crystal surface 602.

The crystal portion 601 is configured so that the light beam 612 is totally internally reflected at the other crystal surfaces 604, 606, 608. Thus, the light beam 612 propagates back and forth within the crystal portion 601 until tissue 213 contacts the first crystal surface 602.

As shown in FIG. 6B, the light beam 612 reflects from the first crystal surface 602 at a first location 621, a second location 622, and a third location 623 as the light beam 612 propagates back and forth within the crystal portion 601. When the first jaw member 110 and second jaw member 120 grasp tissue 213, the tissue 213 makes contact with the first crystal surface 602 at the first location 621 and the second location 622. This creates conditions of frustrated total internal reflection at the first location 621 and the second location 622. As a result, a first portion 615 of the light beam 612 is transmitted through the first location 621 of the first crystal surface 602 to the tissue 213 and a second portion 617 of the light beam 612 is transmitted through the second location 622 to the tissue 213. In this manner, the light beam 612 can be evenly distributed through the tissue 213.

For purposes of safety, the second crystal surface 604 and the third crystal surface 606 are coated with a reflective material 611 to prevent the light beam 612 from being transmitted to tissue or other objects that accidentally come into contact with the second crystal surface 604 and/or the third crystal surface 606. In other embodiments, the second crystal surface 604 and/or the third crystal surface 606 may not be coated with the reflective material 611 to allow the user to perform surgical procedures using the second crystal surface 604 and/or the third crystal surface 606.

As shown in FIGS. 6A and 6B, the second jaw member 120 includes a light-absorbent optical element 620 that absorbs the first portion 615 of the light beam 612 and the second portion 617 of the light beam 612 that pass through the tissue. The light-absorbent optical element 620 is disposed a short distance away from the tissue-contacting surface 212 of the second jaw member 120. In some embodiments, the second jaw member 120 may be a hollow jaw member having an optically-transparent tissue-contacting surface 212, which allows the first portion 615 of the light beam 612 and the second portion 617 of the light beam 612 to pass through the tissue-contacting surface 212 to the light-absorbent optical element 620.

Figure 7:
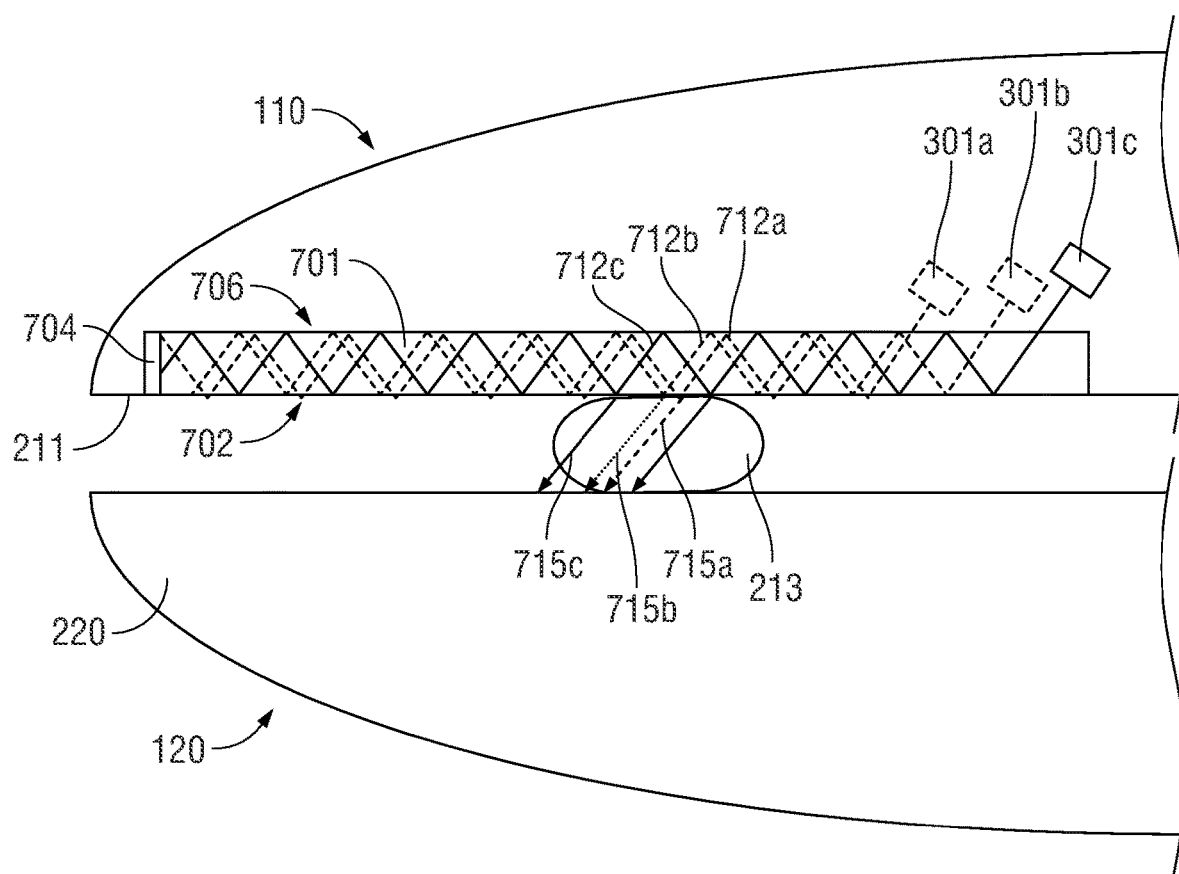
FIG. 7 is a schematic side, cross-sectional view of jaw members, one of which incorporates a light guide, according to embodiments of the present disclosure.

FIG. 7 illustrates another embodiment of the first jaw member 110 and the second jaw member 120. The first jaw member 110 includes a light guide 701 having a first guide surface 702 that forms a portion of the tissue-contacting surface 212 of the first jaw member 110. The first jaw member 110 also includes multiple light sources 301a-301c. The light sources 301a-301c generate multiple light beams 712a-712c that are directed into the light guide 701. The light sources 301a-301c direct the multiple light beams 712a-712c at an appropriate angle with respect to an axis normal to the first guide surface 702 so that the multiple light beams 712a-712c are totally internally reflected off the first guide surface 702 and a second guide surface 706 when tissue does not contact the first guide surface 702.

The light guide 701 includes a light-absorbent optical element 704 at the distal end of the light guide 701. The light-absorbent optical element 704 absorbs the multiple light beams 712a-712c that propagate along the length of the light guide 701. When the tissue 213 comes into contact with the light guide surface 702, portions 715a-715c of the multiple light beams 712a-712c are transmitted through the tissue 213 to heat and seal the tissue 213. In this way, light is distributed across the tissue 213.

As shown in FIG. 7, the multiple light beams 712a-712c reflect off of different portions of the first light guide surface 702 as the multiple light beams 712a-712c propagate along the length of the light guide 701. When the tissue 213 comes into contact with the first light guide surface 702, portions of the multiple light beams 712a-712c are transmitted only through those portions of the first light guide surface 702 that are in contact with the tissue 213. In some embodiments, the multiple light sources 301a-301c may be configured to generate multiple light beams 712a-712c, respectively, having different wavelengths selected to produce a desired tissue affect.

Similar to the second jaw member 120 of FIGS. 2A and 2B, the second jaw member 120 is made of a light-absorbent optical element 220 that absorbs the portions 715a-715c of the multiple light beams 712a-712c that are transmitted through the tissue 213. In other embodiments, the light-absorbent optical element 220 is replaced with a light-reflective optical element, which may reflect the portions 715a-715c of the multiple light beams 712a-712c back into the light guide 701.

In alternative embodiments, the multiple light sources 301a-301c may be replaced by a movable light source. For example, the light source may translate along the length of the light guide 701 to scan multiple portions of the tissue 213 (similar to the movable light source 501 in FIG. 5C).

Figure 8:
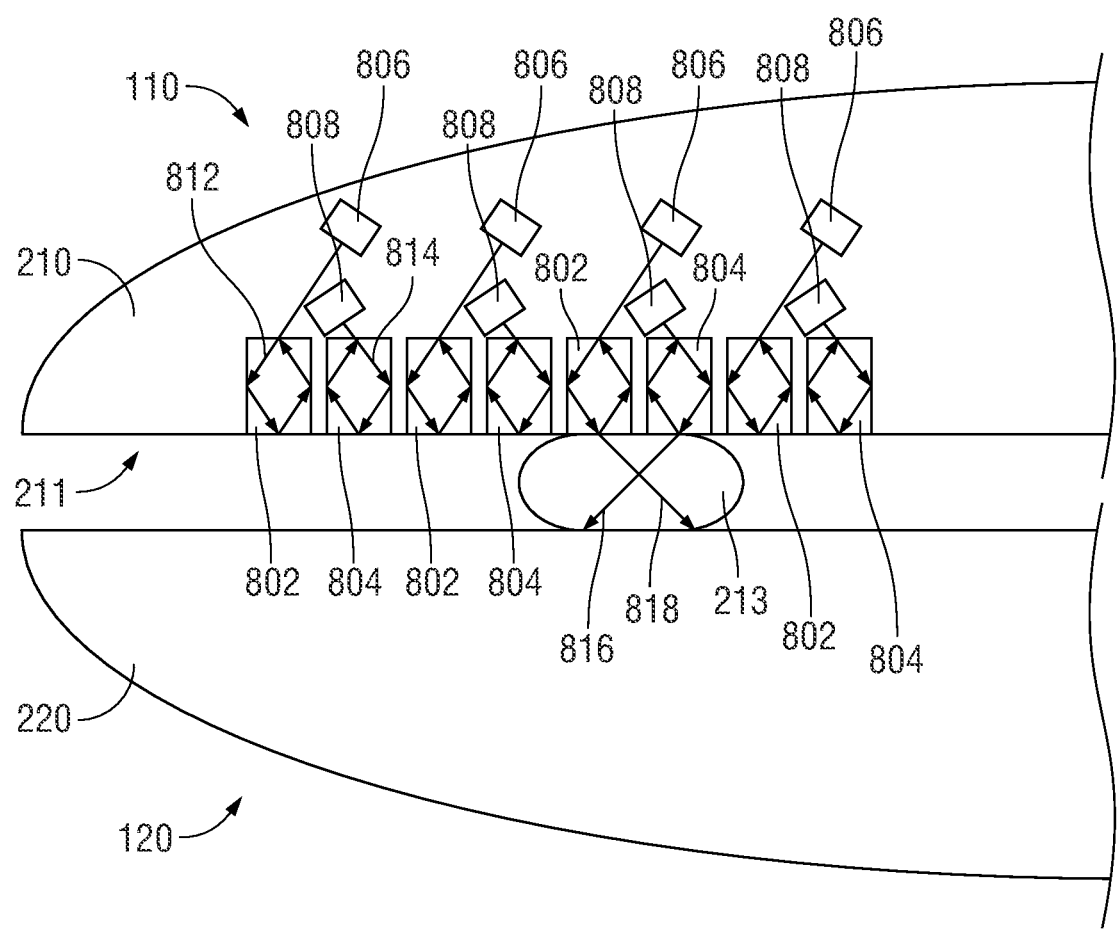
FIG. 8 is a schematic side, cross-sectional view of jaw members, one of which includes a plurality of optical elements according to embodiments of the present disclosure.

FIG. 8 illustrates another embodiment of the first jaw member 110 that incorporates multiple crystals 802, 804. The multiple crystals 802, 804 are distributed along a longitudinal axis of the first jaw member 110 and each crystal 802, 804 includes a first crystal surface that forms a portion of the tissue-contacting surface 211. In other embodiments, the multiple crystals 802, 804 are also distributed in rows along a transverse axis of the first jaw member 110.

The first jaw member 110 also includes multiple light sources 806, 808 that generate light beams 812, 814 and direct them into respective crystals 802. In this embodiment, the light sources 806 direct the light beams 812 at a first angle into the crystals 802 so that the light beams 812 are totally internally reflected and circulate within the crystals 802 in a counter-clockwise direction when tissue is not in contact with the tissue-contacting surfaces of the crystals 802. Similarly, the light sources 808 direct the light beams 814 at a second different angle into the crystals 804 so that the light beams 814 are totally internally reflected and circulate within the crystals 804 in a clockwise direction when tissue is not in contact with the tissue-contacting surfaces of the crystals 804.

As shown in FIG. 8, the light beams 812, 814 are transmitted into the tissue 213 from only those crystals 802, 804 whose first tissue-contacting surfaces come into contact with the tissue 213. And because the light beam 812 is circulating in a different direction from the light beam 814, the transmitted light beams 816, 818 pass through the tissue 213 in different directions.

The optical elements described above may be formed of any material that facilitates total internal reflection. In various embodiments, the optical elements may be formed of sapphire crystal, ruby, YAG, alexandrite, flint, BK7 glass, crystal glass, or fused silica.

Figure 9:
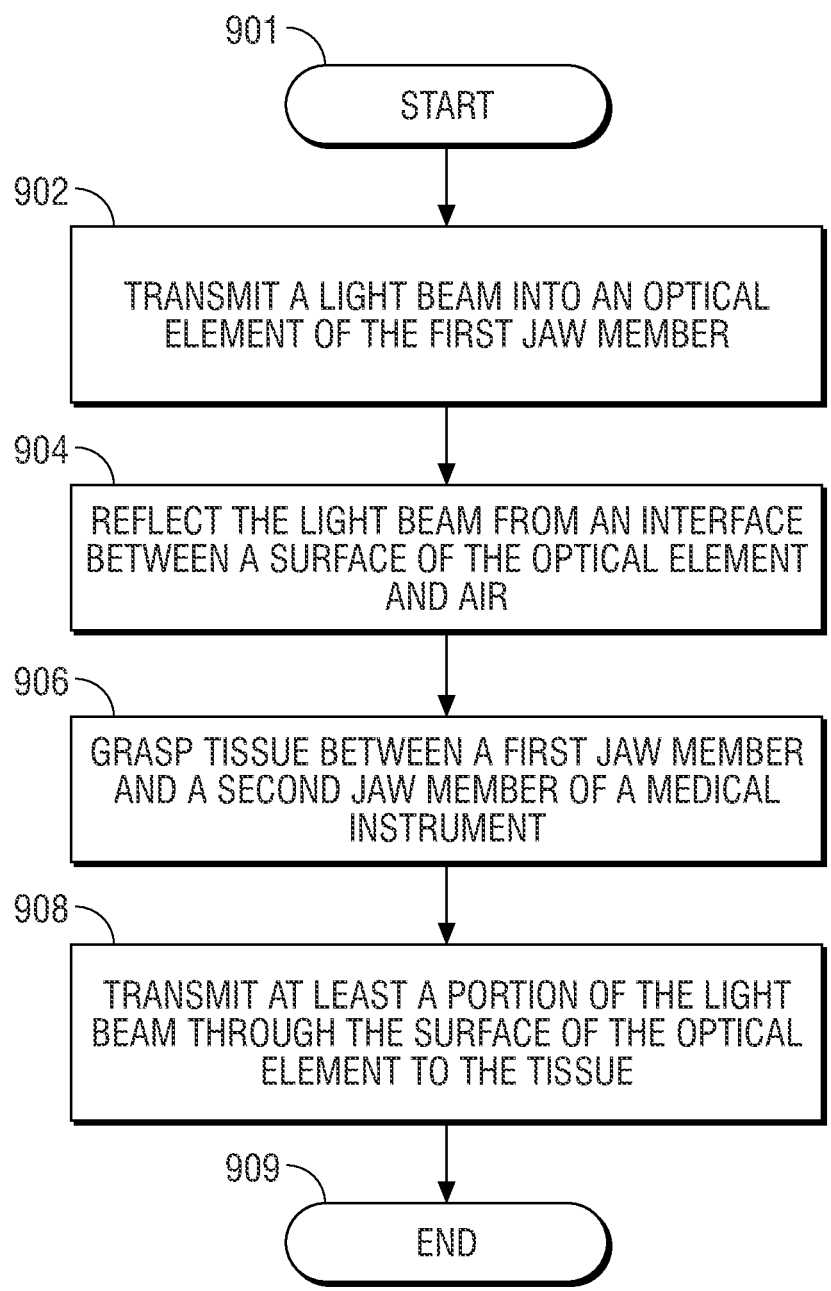
FIGS. 9 and 10 are flow diagrams of methods of performing tissue sealing according to embodiments of the present disclosure.

FIG. 9 is a flow diagram of a method of performing a tissue-sealing procedure with light. After the procedure starts (step 901), tissue is grasped between a first jaw member and a second jaw member of a medical instrument (step 902). Next, a tissue-contacting surface of an optical element of the first jaw member is illuminated with a light beam (step 904). Then, the light beam is reflected from the tissue-contacting surface when tissue does not contact the tissue-contacting surface of the optical element (step 906). Before the method ends (step 909), at least a portion of the light beam is transmitted through the tissue-contacting surface of the optical element when tissue contacts the tissue-contacting surface of the optical element (step 908).

Figure 10:
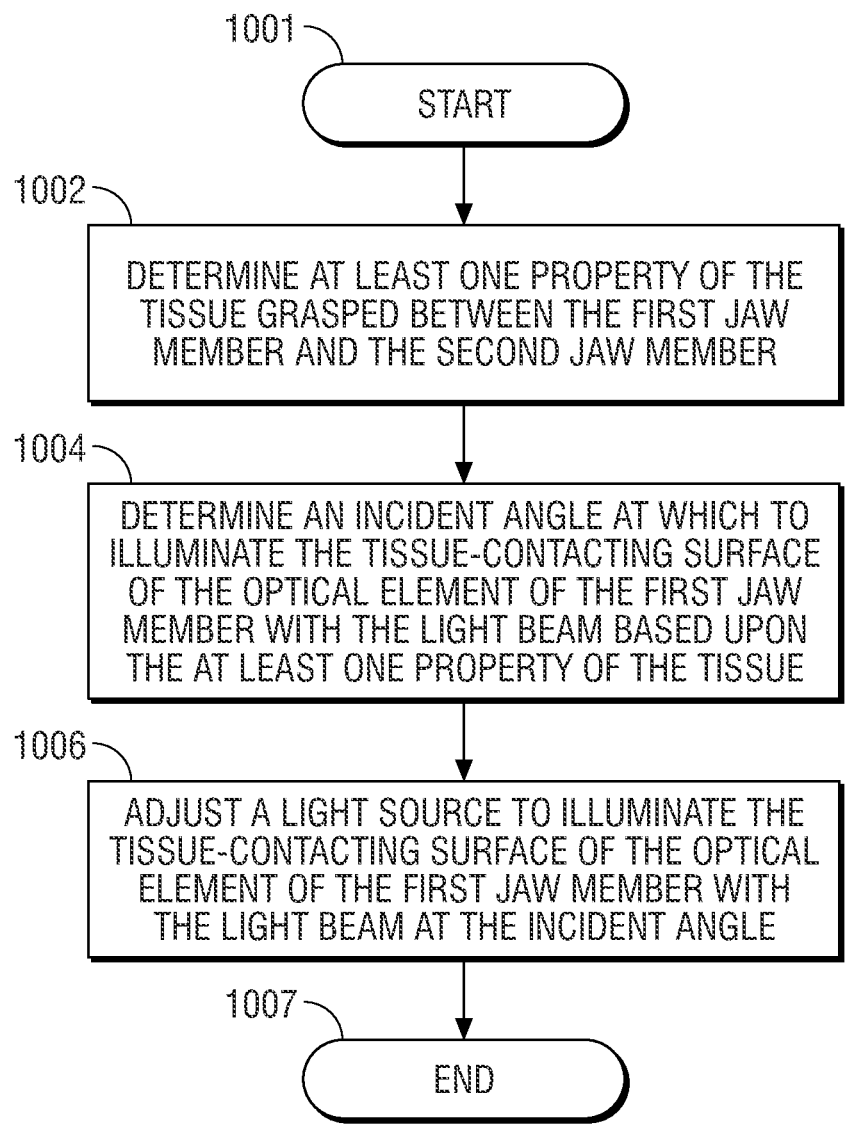

FIG. 10 is a flow diagram of a method of performing a tissue-sealing procedure with light. After starting (step 1001), at least one property of the tissue to be grasped between the first jaw member and the second jaw member is determined (step 1002). Next, an incident angle at which to illuminate the tissue-contacting surface of the optical element of the first jaw member with the light beam is determined based upon the at least one property of the tissue (step 1004). Before the method ends (step 1007), a light source is adjusted to illuminate the tissue-contacting surface of the optical element of the first jaw member with the light beam at the incident angle (step 1006).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A medical instrument, comprising:
a first jaw member having a tissue-contacting surface;
a second jaw member movably coupled to the first jaw member, the first jaw member and the second jaw member cooperating to grasp tissue between the first jaw member and the second jaw member; and
a light source that provides a light beam for sealing tissue, the light source directed at a reflective optical element configured to reflect the light beam towards the tissue-contacting surface of the first jaw member at a predetermined angle of incidence with respect to an axis perpendicular to the tissue-contacting surface of the first jaw member, the predetermined angle of incidence configured to provide total internal reflection of the light beam from any point along an interface between the tissue-contacting surface of the first jaw member and air, and to impede the light beam from transmission through the interface when tissue is not grasped between the first jaw member and the second jaw member, and the predetermined angle of incidence configured to provide transmission of at least a portion of the light beam through a portion of the tissue-contacting surface of the first jaw member that is in contact with the tissue when the tissue is grasped between the first jaw member and the second jaw member.

2. The medical instrument according to claim 1, wherein the light source is selected from the group consisting of an optical fiber, a light-emitting diode, a laser, a diode laser, and a fiber laser.

3. The medical instrument according to claim 1, wherein the second jaw member includes a light-absorbent material that absorbs light that is transmitted through the tissue.

4. The medical instrument according to claim 1, wherein the second jaw member includes a reflective material that reflects light that is transmitted through the tissue.

5. The medical instrument according to claim 1, wherein the light source is movable and is configured to move to a position based on at least one optical property of the tissue while the tissue is in contact with at least a portion of the tissue-contacting surface of the first jaw member.

6. The medical instrument according to claim 1, wherein the light source is rotatable to selectively direct the light beam toward the reflective optical element of the first jaw member at a variable angle of incidence with respect to the axis perpendicular to the tissue-contacting surface of the first jaw member.

7. The medical instrument according to claim 1, further comprising an optical element disposed in the first jaw member, the optical element having a side that forms at least a portion of the tissue-contacting surface of the first jaw member.

8. The medical instrument according to claim 7, wherein the optical element is a light guide that extends along at least a portion of a longitudinal axis of the first jaw member.

9. The medical instrument according to claim 8, wherein a light-absorbent element or a light-reflective element is coupled to at least a portion of a distal portion of the light guide.

10. The medical instrument according to claim 7, wherein the optical element is a crystal configured to circulate the light beam provided by the light source when the tissue is not grasped between the first jaw member and the second jaw member.

11. The medical instrument according to claim 7, wherein the optical element is formed of a material selected from the group consisting of sapphire, ruby, YAG, alexandrite, flint, BK7 glass, and fused silica.

12. The medical instrument according to claim 7, wherein the second jaw member includes a second optical element having a side that forms at least a portion of a second tissue-contacting surface, and further comprising a second light source that provides a second light beam for sealing tissue, the second light source optically coupled to the second optical element so that the second light beam is totally internally reflected from the interface between the second tissue-contacting surface of the second optical element and air when tissue is not grasped between the first jaw member and the second jaw member, and so that at least a portion of the second light beam is transmitted through a portion of the second tissue-contacting surface that is in contact with the tissue when the tissue is grasped between the first jaw member and the second jaw member.

13. The medical instrument according to claim 7, wherein the first jaw member is hollow and the optical element is disposed therein.

14. The medical instrument according to claim 7, wherein the optical element forms at least a portion of the first jaw member.

15. An optical-based tissue-sealing system, comprising:
a housing;
an end effector assembly operably connected to the housing, the end effector assembly including:
    a first jaw member having a tissue-contacting surface, and
    a second jaw member movably coupled to the first jaw member, the first jaw member and the second jaw member cooperating to grasp tissue between the first jaw member and the second jaw member;
a light source that provides a light beam for sealing tissue, the light source directed at a reflective optical element configured to reflect the light beam towards the tissue-contacting surface of the first jaw member at a predetermined angle of incidence with respect to an axis perpendicular to the tissue-contacting surface of the first jaw member, the predetermined angle of incidence configured to provide total internal reflection of the light beam from any point along an interface between the tissue-contacting surface of the first jaw member and air, and to impede the light beam from transmission through the interface when tissue is not grasped between the first jaw member and the second jaw member, and the predetermined angle of incidence configured to provide transmission of at least a portion of the light beam through a portion of the tissue-contacting surface of the first jaw member that is in contact with the tissue when the tissue is grasped between the first jaw member and the second jaw member; and
a controller coupled to the light source, the controller configured to control at least one parameter of the light beam.

16. The optical-based tissue-sealing system according to claim 15, wherein the at least one parameter of the light beam is selected from the group consisting of intensity, wavelength, polarization, and angle of incidence with respect to the axis perpendicular to the tissue-contacting surface of the first jaw member.

17. The optical-based tissue-sealing system according to claim 15, further comprising a sensor configured to sense at least one optical property of the tissue, wherein the controller is configured to control at least one parameter of the light beam based upon the at least one optical property of the tissue.

18. A method of treating tissue with an optical energy-based medical instrument, comprising:
reflecting a light beam, by a reflective optical element, into an optical element of a first jaw member of an optical energy-based instrument and toward a tissue contacting surface of the optical element at a predetermined angle of incidence with respect to an axis perpendicular to the tissue contacting surface of the optical element, the light beam provided by a light source directed at the reflective optical element;
totally internally reflecting the light beam within the optical element from any point along an interface between the tissue-contacting surface of the optical element and a media having a low index of refraction, and impeding the light beam from transmission through the interface when tissue is not grasped between the first jaw member and a second jaw member;
grasping tissue between the first jaw member and the second jaw member of the optical energy-based medical instrument; and
transmitting at least a portion of the light beam through a portion of the tissue-contacting surface of the optical element to the tissue when the tissue is grasped between the first jaw member and the second jaw member.

19. The method according to claim 18, further comprising controlling at least one parameter of the light beam.

20. The method according to claim 19, wherein the at least one parameter of the light beam is selected from the group consisting of intensity, wavelength, polarization, and angle of incidence with respect to the axis perpendicular to the tissue-contacting surface of the first jaw member.

* * * * *